United States Patent [19]

Charlton et al.

[11] Patent Number: 5,470,881
[45] Date of Patent: Nov. 28, 1995

[54] UREA OPHTHALMIC OINTMENT AND SOLUTION

[75] Inventors: Judie F. Charlton, Morgantown, W. Va.; Ivan R. Schwab, Sacramento, Calif.; Robert M. Stuchell, Morgantown, W. Va.

[73] Assignee: West Virginia University Research Corporation

[21] Appl. No.: 118,265

[22] Filed: Sep. 9, 1993

[51] Int. Cl.$^6$ .................................................. A61K 31/17
[52] U.S. Cl. ........................................... 514/588; 514/912
[58] Field of Search ..................................... 514/588, 912

[56] References Cited

U.S. PATENT DOCUMENTS 4,409,205  10/1983  Shively ........................................ 424/78

OTHER PUBLICATIONS

Ashton H. et al., Therapeutics XIII Urea as a Topical Agent, Quarterly Review, BR J Dermatol 84:194, 1970.
Lars Hellgren and Kare Larsson, "On the Effect of Urea on Human Epidermis", Dermatologica 149:289–293 (1974).
Gunnar Swanbeck, "A New Treatment of Ichthyosis and Other Hyperkeratotic Conditions", Acta derm.–venerol. 48:123–127, 1968.
Jorn Hess Thaysen and Niels A. Thorn, "Excretion of Urea, Sodium, Potassium and Chloride in Human Tears", American Journal of Physiology 178:160–164, 1954.
W. P. Raab, "Uses of Urea in Cosmetology", Cosmetics and Toiletries, vol. 105, pp. 97–102 (May 1990).
Paritosh K. Banerjee, et al., "Topical Urea in Dermatology", Indian J. Dermatology, vol. 35, No. 1, Mar. 1990 48:123–127, 1968.
Toshiaki Nishihata, et al., "Combined Effect of Alcohol and Urea on the In Vitro Transport of Indomethacin across Rat Dorsal Skin", Journal of Pharmaceutical Sciences, vol. 79, No. 6, Jun. 1990.
The Merck Index, "An Encyclopedia of Chemicals, Drugs, and Biologicals", Eleventh Edition, pp. 44 and 1553 (1989).
Altwein, et al., "Effect of Urea Concentrations on the Solubility of the Isometric Monohydroxybenzoic Acids", Journal of Pharmaceutical Sciences, vol. 54, No. 4, pp. 603–606 (Apr. 1965).
American Hospital Formulary Service, 40:28 Diuretics, pp. 1362–1364 1987.
Gilbard, et al., "Morphologic Effect of Hypersmolarity on Rabbit Corneal Epithelium", Ophthalmology 91:1205–1212, 1984.
Socma Handbook, "Commercial Organic Chemical Names", p. 195 (1965).
Connors, et al., "Chemical Stability of Pharmaceuticals", a Handbook for Pharmacists, Second Edition, pp. 780–786 (1986).
Sigma, "Biochemicals Organic Compounds—Diagnostic Reagents", Order Form and Price List pp. 202, 1000–1001, (1994).
Aldrich Chemical Company, Inc., Order Form and Price List, 1992.
Sanford Bolton, "Interaction of Urea and Thiourea with Benzoic and Salicylic Acids", Journal of Pharmaceutical Science, vol. 52, No. 11, Nov. 1963, pp. 1071–1074.
Apple, et al., "Clinicopathologic Correlation of Ocular Disease", Second Edition, 1978, pp. 456–457.
Yanoff, et al., "Ocular Pathology", Second Edition, 1982, p. 318.
Embase Abstract by Opthamologica, 1979, (198–203) Danopoulos et al.

*Primary Examiner*—Zohreh Fay
*Attorney, Agent, or Firm*—Cushman Darby & Cushman

[57] ABSTRACT

A topical ophthalmic preparation utilizing a urea and/or urea derivative or mixtures thereof as the principle active ingredient within a range of about 0.01% by weight to about 30% by weight and a method of using the same. When applied to a mammalian eye affected with an abnormal ophthalmological surface problem resulting in epithelial cell loss, keratinization, and/or scarring, the present invention will heal epithelial defects, soften keratin, decrease scarring, enhance hydration, and have anti-mucolytic activity. The present invention provides a method for treating ocular conditions such as dryness, noninfectious keratitis, corneal or conjunctival epithelial irregularities, ocular scarring and subjective irritations.

9 Claims, No Drawings

UREA OPHTHALMIC OINTMENT AND SOLUTION

The present invention relates generally to urea and/or urea derivative preparations for use in multi-purpose ophthalmic solutions or ointments suitable for topical ocular use in mammalian eyes.

Specifically, the present invention relates to a topical ocular preparation utilizing urea or its derivatives as an active agent to treat ocular surface abnormalities which include, among other things, loss of epithelial cells, keratinization, and scarring. It is suitable for decreasing subjective ocular irritation. This invention also may be used for decreasing ocular scarring post-operatively or following trauma. The present invention also relates generally to enhancing healing of the ocular epithelial surface.

Urea has been used in the treatment of skin and is known in treating skin to have the properties of softening keratin, increasing hydration, promoting epithelization, decreasing fibroblast action, and having mucolytic properties. However, urea has not been used in the treatment of eye related disorders. One of the reasons urea has not been used in treating eye disorders is that it will hydrolyze in aqueous vehicles thus producing ammonia as a byproduct. Ammonia is toxic to the eye, and thus urea in an aqueous solution would be impractical for use as an ophthalmic medicament. To use urea's desired healing effect, it may be formulated in ointment or sustained release form for delivery to the ocular surface. Urea derivatives are more stable in aqueous solution and may therefore be formulated in solution, ointment, or sustained release delivery systems. Preparation of the contemplated preparation is carried out by dissolution of urea crystals, complexation of the urea to another chemical entity if desired, and incorporation into a suitable ophthalmic vehicle.

This invention relates to a unique ophthalmic topical preparation which is designed for general use in mammalian eyes, but is especially adapted for use in normalizing irregular surface structure in the eyes of humans and domestic animals. The ocular surface is normally covered by non-keratinized, squamous epithelium; it is the most regularly arranged of all squamous epithelia in the body. The ocular surface can be disrupted which results in loss of epithelial cells and/or keratinization. Events which can cause such surface disruption include, e.g., trauma, exposure, chemical toxicity, surgery, and bacterial or viral infection. Ocular conditions which cause such cell loss and keratinization include, e.g., dry eye, inherited dystrophies, degenerations, corneal erosion syndrome, and allergies. When the ocular surface undergoes such changes, the eye becomes irritated and often produces excessive mucus. Following surgery or ocular surface damage, increased fibroblast activity and scarring can occur which may result in visual loss (opacification of the corneal surface) or poor results following ocular surgery. Properties of urea that make it useful in treating ocular surface problems include that it softens keratin (keratolytic), promotes epithelialization, decreases fibroblast action, promotes hydration, and is anti-mucolytic.

Dry eye and irritated eyes are usually treated by applying a slightly viscous polymer solution in drop form to the eye to provide temporary wetting before the solution evaporates or is wiped away by blinking. Since the polymer solutions tend to be cleared from the eye rather quickly, frequent dosing may be required.

The present invention discloses the use of urea and/or urea derivative preparations for use in multi-purpose ophthalmic solutions or ointments, suitable for topical ocular use in the eyes of both humans and animals. It also discloses the use of urea in ophthalmic ointments or sustained release delivery form. Studies show the urea preparations disclosed herein to be superior to the current agents on the market used for treating dry eye. Current agents merely mimic normal human tears by making small changes such as decreasing solution osmolarity and increasing viscosity. The agents used in these existing preparations have no healing activity on the cellular structures of the eye. In contrast, the present invention has the beneficial property of promoting epithelization, promoting hydration, decreasing fibroblast action, and softening the cellular product keratin. Thus, the present invention has a wide variety of therapeutic uses in treating common eye problems. These problems broadly include causes of ocular surface epithelial cell loss, keratinization, and scarring. Conditions which cause such problems include, e.g., dry eye (keratoconjunctivitis sicca), contact lens related keratoconjunctivitis, recurrent erosion syndrome, bullous keratopathy, filamentary keratitis, and post-surgical keratoconjunctivitis. Corneal abrasions are another common eye condition which benefit from the present invention's ability to promote epithelialization. Ocular surgeries which have the postoperative healing enhanced by topical use of the present invention include glaucoma, cataract, and corneal surgeries. Glaucoma surgery in particular benefits from the ability of the present invention to decrease fibroblastic activity which promotes and maintains the desired conjunctival bleb formation.

DESCRIPTION OF THE PRIOR ART

Ophthalmic solutions have been previously developed for treating dry eye by mimicking normal human tears. Such formulations are usually isotonic or mildly hypotonic utilizing sodium or potassium salts and having increased viscosity to increase ocular retention time.

Ophthalmic solutions having been previously developed for treating "dry eye" syndrome and for use as lubricating and cushioning agents for eyes subject to traumatic injury, contact lens irritation or surgery. Such solutions have generally been buffered to a physiologic pH, made isotonic or mildly hypotonic, and contained various synthetic polymers as essential additives for improved viscosity and longer retention in the eye.

U.S. Pat. No. 3,767,788 to Rankin, for example, discloses one such solution which includes as an essential additive a high molecular weight ethylene oxide, polymer ether, such as polyethylene oxide or polyethylene glycol, as a humectant. Various biocide preservations and tonicity adjusting agents may be combined. The principle ingredient, the polyethylene oxide polymer, has lubricating and viscosity enhancing properties. These ingredients help compensate for the lack of normal tears in a dry eye condition, but these ingredients have no direct affect on cellular activity. The present invention in contrast has been shown to promote growth of epithelial cells (which enhances healing) and to decrease activity of fibroblasts (which decreases scarring). The present invention also has the added properties of softening keratin and antipruritic activity.

U.S. Pat. No. 3,907,985 to Rankin discloses another ophthalmic solution which is said to be effective in treating dry eye conditions, and includes polystyrene sulfonate as an essential ingredient. Again, this ingredient functions as a lubricant and viscosity enhancing agent.

U.S. Pat. No. 4,039,662 to Hecht et al. describes an ophthalmic solution containing a particular polysaccharide and benzalkonium chloride which together apparently produce a synergistic effect and provide a synthetic tear film component which in-parts a mucin-like layer to the cornea. This enhances wetting of the eye and helps decrease tear/solution evaporation. Again, these ingredients have no direct beneficial effect on the ocular epithelial or fibroblast cells.

U.S. Pat. No. 4,300,557 to Refajo discloses a method for treating intraocular malignancies with a constant diffusion of solution containing nitrosourea. A surgically implanted capsule allows lipid soluble products containing nitrosourea to access the eye over prolonged periods. Trials of the drug demonstrated slowing of tumor growth and particular effectiveness when combined with ethanol. This patent does not disclose the use of urea, and the advantages of the present invention for treating dry eyes. Nitrosourea (BCNU) is an anti-metabolite which is caustic to the eye yet effective against cancerous tumors.

U.S. Pat. No. 4,409,205 to Shively discloses an ophthalmic solution for normalizing an irregularly structured tear film, wherein the amount of ionic salt (such as sodium) in the solution is kept within the range of 0.01% to 7.5%. A non-ionic, non-charged, tonicity adjusting agent is to be used which may be selected from group consisting of mannitol, sorbitol, dextrose, sucrose, urea, glycerol and mixtures of those listed. Only dextrose is mentioned in the examples. This patent teaches that the addition of tonicity adjusting agents, in concentrations of from 0.5% to 5%, retards the precipitation of dehydrated protein-like substances in the tears and promotes the resolubilization of such substances. According to Shively it is not possible to achieve this effect when using previously known ophthalmic solutions containing relatively high amounts of ionic salt ions. When utilizing urea as an aqueous solution in the pH range described by Shively, the urea would be expected to hydrolyze, thus producing ammonia as a by-product. Ammonia is toxic to the ocular surface, and thus Shively's invention using urea would be expected to be toxic to the ocular surface.

U.S. Pat. No. 4,539,330 to Trager et al. discloses ophthalmic solutions containing imidazolidinyl urea or imidazolidinyl urea derivatives. Use of these urea derivatives in ophthalmic solutions imparts antimicrobial or preservative properties. The urea derivatives were considered to be an effective preservative for contact lens solution, artificial tears formulations, and for medicament delivery systems. This patent discloses that urea derivatives may be employed by concentrations from about 0.01% to about 3% by weight. A 0.3% solution of the imidazolidinyl urea was considered effective with the pH of 7.2. These urea derivatives were only described to have antimicrobial activity. Due to the molecular size of the imidazolidine and/or its derivatives, the surface healing activity of the urea would be lost. Thus the invention described by Trager would not be expected to have the ocular enhancement properties as described by this invention.

U.S. Pat. No. 4,818,537 to Guo discloses a treatment for dry eyes with an aqueous suspension of liposomes. Liposomes are microcapsules which contain solutions or drugs and slowly release their contents in a long-acting, sustained release fashion. When liposomes are put into suspension in an ophthalmic solution, they may slowly release their contents thus providing a longer contact time with the eye. In this patent, the liposome capsule composition consisted of mostly hydrogenated phosphatidylcholine. The contents of the liposome are to contain aqueous fluid, film-forming lipids, Vitamin A, and/or a bacteriostatic agent. According to Guo, this delivery system provides increased duration of delivering aqueous fluid to the eye, muco-mimetic properties to form a stable tear film, and decreased need for frequent dosing.

It has commonly been accepted in the art that to treat ocular surface diseases such as dry eye and other causes of non-infectious keratitis, agents should be used which mimic natural tears. Such agents generally include near isotonic levels of monovalent cation containing salts, principally sodium and potassium ions. These preparations generally also include some agent which increases viscosity and surface wetting. Tonicity, pH, and antimicrobial agents are also commonly added. No preparation has been described which directly enhances hydration and affects the cells of the ocular surface.

Generally, these prior art attempts have not resulted in a truly new novel active ingredient for treating ocular surface problems. They merely mimic normal tears while making some modest modifications.

In summary, prior art endeavors in this field have fallen short because no active ingredient has been identified which directly affects the healing process.

Hyperosmolar solutions are known to cause ocular surface damage when applied topically. A preferred embodiment of the present invention was administered to rabbit eyes which had epithelial defects and keratinization. Even when formulated in a hyperosmolar state, the ocular surface receiving this invention healed more quickly than the fellow control eyes. This was surprising and unexpected in that hyperosmolar solutions would have been expected to either worsen or delay the healing of the condition.

The concept of administering hyperosmolar urea solutions to the eye came about when it was unexpectedly observed that renal dialysis patients have hyperosmolar tears due to high concentrations of urea, yet have no subjective complaints of dry eye nor many physical ocular findings consistent with dry eye. Based on this unexpected observation, it has now been discovered that utilizing urea or its derivative as the primary active ingredient is effective in treating ocular surface problems of keratinization, epithelial loss, and scarring. With respect to the treatment of skin, urea is known to have properties of softening keratin, increasing hydration, promoting epithelization, decreasing fibroblast action, and having mucolytic properties. It has now been unexpectedly discovered that urea may be safely added to the eyes of mammals in the present invention and result in promotion of ocular surface healing.

The present invention meets this need by providing urea preparations for treating eye conditions which result in keratitis, epithelial cell loss, and scarring such as dry eye, toxic, allergic, infectious, or exposure keratitis. Corneal abrasions, recurrent corneal erosions, and post-surgical eyes also benefit from treatment with the present invention.

SUMMARY OF THE DISCLOSURE

In its broadest sense, the present invention provides a topical ophthalmic preparation utilizing urea or its derivative as the principle active ingredient within a range of about 0.01% by weight to about 30% by weight and a method of using the same. When applied to an uncomfortable, irritated eye with keratitis, epithelial cell loss, or scarring, the medication helps to heal the epithelial defects, soften keratin, decrease scarring, enhance hydration, and have anti-mucolytic activity.

Thus, it is in keeping with the overall concept of this invention that its object is to provide an ophthalmic preparation which when topically applied to an eye affected with an abnormal ophthalmological surface problem which results in epithelial cell loss, keratinization, and/or scarring, the present invention will promote epithelial healing.

It is also a principle object of the invention to provide a method for treating ocular conditions such as dryness, noninfectious keratitis, corneal or conjunctival epithelial irregularities, ocular scarring and subjective irritations which comprises applying to the ocular surface of a mammalian eye an ophthalmic ointment utilizing urea and/or urea derivatives or mixtures thereof.

It is also an object of the invention to provide a method for treating ocular conditions such as dryness, noninfectious keratitis, corneal or conjunctival epithelial irregularities, ocular scarring and subjective irritations which comprises applying to the ocular surface of a mammalian eye an ophthalmic preparation utilizing a urea derivative or mixtures of urea derivatives.

An additional object of the invention is to provide a method for promoting epithelialization, promoting hydration, decreasing fibroblast action and softening keratin which comprises applying to the ocular surface of a mammalian eye an ophthalmic ointment utilizing urea and/or urea derivatives or mixtures thereof.

Another object of the invention to provide a method for promoting epithelialization, promoting hydration, decreasing fibroblast action and softening keratin which comprises applying to the ocular surface of a mammalian eye an ophthalmic preparation utilizing a urea derivative or mixtures of urea derivatives.

A further object of the invention is to provide a method for treating ocular conditions such as dryness, noninfectious keratitis, corneal or conjunctival epithelial irregularities, ocular scarring and subjective irritations which comprises topical ocular application of a hyperosmolar preparation utilizing a urea derivative or mixtures of urea derivatives.

It is also an object of the invention to provide a topical ophthalmic ointment utilizing urea and/or urea derivatives or mixtures thereof. It is a further object of the invention to provide a topical ophthalmic preparation utilizing a urea derivative or mixtures of urea derivatives.

It is another object of the invention to provide an ophthalmic preparation which will help to soften keratin on the ocular surface.

It is another object of the invention to provide an ophthalmic preparation which when applied to the eye of a human, will decrease fibroblast activity to decrease scarring.

It is an additional object of the invention to provide an ophthalmic preparation which will be useful in reducing minor eye irritations through its mucolytic and hydration promoting properties.

The manner in which these and other objects of the present invention are more concisely demonstrated, and a greater appreciation of the invention realized, can be ascertained from the following detailed description and accompanying claims.

DETAILED DESCRIPTION OF THE PREFERRED EMBODIMENTS

As noted above, the present invention relates to the use of urea preparations for use in multi-purpose ophthalmic preparations, suitable for topical ocular use in mammalian eyes. All of the percentages (%) recited in this application are "by weight" unless otherwise indicated.

The present invention comprises an ophthalmic solution using urea or its derivative as the principal active ingredient within the range of about 0.01% to about 30%. A preferred range would be from 0.1% to 20%. A more preferred range would be from 1% to 10%. A most preferred range would be from 2 to 5%. When a urea complex is utilized, the percentage of the complex weight in the final preparation will be proportional to allow for the weight of the molecule added to urea.

Urea (also known commercially as carbamide) may be utilized in its pure pharmaceutical form or any of its derivative forms (such as being complexed or matrixed with other molecules). Commercially available urea derivatives that may work include urea-D glucuronic acid, allantinon (5-ureidohydantoin), urea phosphate, urea sulfate, ureidoglycolic acid (glyoxylurea), ureidopropionic acid (N-Carbamyl-B-alanine), ureidosuccinic acid (N-Carbamyl-aspartic acid), N-Carbamyl-arginine, N-carbamylglycine (hydantoic acid), or N-carbamyl-phenylalanine. Urea may be complexed to larger molecules such as sulfonamides, wool fat alcohols, or quinoxaline.

The preparation of urea derivatives may be formulated in an ophthalmically acceptable aqueous solutions, ointment, or sustained release topical vehicle. The preparation of urea may be formulated in an ointment or sustained release topical vehicle. For example, an appropriate ointment vehicle would consist of petrolatum, mineral oil and/or anhydrous liquid lanolin. Sustained release vehicles such as liposomes, membrane or contact lens delivery systems, or gel-forming plastic polymers would also be suitable delivery vehicles.

The preparation may contain a non-ionic synthetic polymer such as polyvinyl alcohol, polyethylene glycol or cellulose derivative to increase the viscosity. A preferred viscosity range is 1 cps to 150 cps. A more preferred viscosity range is 50 to 100 cps.

In any of the above formulations, a biocide/preservative may be included. Such ingredients would be compatible with the eye, such as benzalkonium chloride, thimerosal, chlorobutanol, methylparaben, propylparaben or polyquaternium.

Tonicity adjusting agents may be included, such as sodium salts, potassium salts, mannitol, sorbitol, or glycerol. A preferred range is tonicity adjusted from 150 mOsm to 500 mOsm. A more preferred range is 200 mOsm to 400 mOsm.

Suitable chelating agents such as di-,tri-, or tetrasodium diamine ethylene may be included. The pH may be adjusted as desired, but will usually range from four to ten. A more preferred range is 5 to 8.5. A most preferred pH range is 6 to 8.

Compatible, conventional buffers, such as weak acids or alkaline salts of phosphate, borate, citrate, acetate, bicarbonate or other weak bases may be used to adjust and maintain the pH of the preparation.

Essentially any solution forming technique may be utilized in preparing the aqueous ophthalmological preparation of this invention, and when so formed they may be applied to the eye with any known means. Preferably, the application will be in drop form in a manner typically used, for example, to apply eye drops. Thus, the normal squeeze type liquid drop application devices are perfectly suitable for use in applying the ophthalmic solutions of this invention to an eye intended for treatment. The ointment could be delivered in the typical squeezable tube common to today's market.

For a clear understanding of the invention, specific examples of it are set forth below. These examples are merely illustrative and are not to be understood as limiting the scope and underlying principals of the invention in any way. All parts and percentages referred to in this specification and the appended claims are by weight unless otherwise specified.

EXAMPLE I

A urea ophthalmic ointment was prepared based on the following formulation:

| Ingredient | % Weight/Volume |
| --- | --- |
| Water | 3.2% |
| 80% White Petrolatum | 91% |
| 20% Mineral Oil | 2.9% |
| Anhydrous Liquid Lanolin | 2.9% |
| Urea | 2.24% |

Urea ophthalmic ointment was compounded by dissolving urea crystals in distilled water and incorporating the solution into an ophthalmic ointment vehicle consisting of white petrolatum, (94%), mineral oil (3%) and anhydrous liquid lanolin (3%) (Duratears, Alcon Laboratories). The final concentration of the urea was 2.24%. The final osmolarity of the preparation was 370 mOsm (308 mOsm is isotonic).

Toxic keratitis was induced in 12 rabbits with 0.5% benzalkonium chloride solution. Each rabbit was randomly assigned to receive urea ointment in one eye and control ophthalmic ointment in the other eye.

The control ointment consisted of the petrolatum, mineral oil, and anhydrous liquid lanolin base with 3.2% ml of artificial tears incorporated. (The ointment base was clear however, when solution was incorporated, whether the solution contained urea or not, the ointment became opaque. The artificial tears were therefore incorporated into the control so that both ointments would be opaque.) The ointment was administered twice daily for 11 days. The observer and person administering the ointment were masked.

The rabbits were examined daily and the corneas were graded according to the following scale.

Decrease in epithelial defect size by 30%

3 plus keratitis 2 plus keratitis 1 plus keratitis trace keratitis no keratitis

One point was awarded for each step of improvement. Intraocular pressure utilizing pneumotonometry was measured prior before and upon completion of the study. Lens clarity was also evaluated at the beginning and end of the study.

Upon completion of the study, the eyes receiving the above urea formulation were noted to improve an average of 5.7 points while the control eyes improved an average of 4.2 points. This was statistically significant to a p less than 0.0001 using a T-test. The decrease in epithelial defect size demonstrates that the present invention promotes growth of epithelial cells. Intraocular pressure did not increase during the study. No lens opacity developed during the course of the study.

EXAMPLE 2

Another example of this invention prepared as a topical solution is described in the following formulation:

| Ingredient | % Weight/Volume |
| --- | --- |
| ureidopropionic acid | 3.0% |
| polyvinyl alcohol | 1.4% |
| chlorobutanol (biocide) | 0.5% |
| sterile water | 93.57% |
| sodium acetate trihydrate (buffer) | 0.39% |
| sodium citrate dihydrate (buffer) | 0.17% | pH adjusted to 7.0 with dilute NaOH or hydrochloric acid at room temperature. Tonicity is adjusted with mannitol to 300 mOsm.

EXAMPLE 3

An ophthalmic topical solution utilizing a urea derivative is illustrated by the below formulation:

| Ingredient | % Weight/Volume |
| --- | --- |
| allantoin | 5% |
| polyvinyl alcohol | 1.4% |
| chlorobutanol | 0.5% |
| NaCl | 0.85% |
| water | 92.25% | pH buffered to 7.0 with NaOH or hydrochloric acid. Tonicity is adjusted with mannitol to 300 mOsm.

It should be understood that this invention may be embodied by specific forms departing from its spirit or essential characteristics. Accordingly, the present embodiments are to be considered in all respects as illustrative and not restrictive. The scope of the invention is being indicated by the appended claims rather than the foregoing description, and all changes which come within the meaning and range of the equivalency of the claims are intended to be embraced therein.

What is claimed:

1. A method for treating ocular conditions selected from the group consisting of dryness, noninfectious keratitis, and corneal or conjuctival epithelial irregularities, the method comprising the steps of:

applying to the ocular surface of a mammalian eye an ophthalmic ointment comprising urea and/or urea derivatives or mixtures thereof.

2. A method for treating ocular conditions selected from the group consisting of dryness, noninfectious keratitis, and corneal or conjuctival epithelial irregularities, the method comprising the steps of:

applying to the ocular surface of a mammalian eye an ophthalmic ointment comprising a urea derivative or mixtures of urea derivatives.

3. A method according to claim 1 wherein the urea and/or urea derivatives or mixtures thereof are about 0.1% to about 30% of the ophthalmic ointment.

4. A method according to claim 1 wherein the urea and/or urea derivatives or mixtures thereof are about 1% to about 10% of the ophthalmic ointment.

5. A method according to claim 1 wherein the urea and/or urea derivatives or mixtures thereof are about 2% to about 5% of the ophthalmic ointment.

6. The method according to claim 1, wherein the urea and/or urea derivatives are formulated in a time release vehicle in the ophthalmic ointment.

7. A method according to claim 2 wherein the urea derivative or mixtures of the urea derivatives are about 0.1% to about 30% of the ophthalmic preparation.

8. A method according to claim 2 wherein the urea derivative or mixtures of the urea derivatives are about 1% to about 10% of the ophthalmic preparation.

9. A method according to claim 2 wherein the urea derivative or mixtures of the urea derivatives are about 2% to about 5% of the ophthalmic preparation.

\* \* \* \* \*